United States Patent
Mozdy et al.

(10) Patent No.: US 7,368,281 B2
(45) Date of Patent: May 6, 2008

(54) LABEL-FREE EVANESCENT-FIELD DETECTION OF BIOLOGICAL AND CHEMICAL AGENTS

(75) Inventors: Eric J. Mozdy, Elmira, NY (US); Frederic J-Y Quan, Corning, NY (US); Po Ki Yuen, Corning, NY (US)

(73) Assignee: Corning Incorporated, Corning, NY (US)

(*) Notice: Subject to any disclaimer, the term of this patent is extended or adjusted under 35 U.S.C. 154(b) by 563 days.

(21) Appl. No.: 10/794,937

(22) Filed: Mar. 5, 2004

(65) Prior Publication Data

US 2004/0191765 A1    Sep. 30, 2004

Related U.S. Application Data

(60) Provisional application No. 60/458,119, filed on Mar. 27, 2003.

(51) Int. Cl.
*C12M 1/34* (2006.01)
(52) U.S. Cl. .......... 435/287.2; 385/12; 385/30; 422/82.05; 422/82.11; 435/6; 435/5; 435/287.9; 435/288.7; 435/808; 436/514; 436/524; 436/525; 436/527; 436/528; 436/529; 436/805
(58) Field of Classification Search .......... 385/12, 385/30; 422/82.05, 82.11; 435/6, 4, 5, 287.2, 435/287.9, 288.7, 808; 436/514, 524, 525, 436/527, 528, 529, 805
See application file for complete search history.

(56) References Cited

U.S. PATENT DOCUMENTS

| | | | |
|---|---|---|---|
| 4,815,843 A | 3/1989 | Tiefenthaler et al. | 356/128 |
| 5,071,248 A | 12/1991 | Tiefenthaler et al. | 356/128 |
| 5,804,384 A | 9/1998 | Müller et al. | 435/6 |
| 5,965,456 A * | 10/1999 | Malmqvist et al. | 436/514 |
| 6,192,168 B1 * | 2/2001 | Feldstein et al. | 385/12 |

(Continued)

FOREIGN PATENT DOCUMENTS

WO   WO 00/40334   7/2000

(Continued)

OTHER PUBLICATIONS

G. Voirin et al., "High-Sensitivity Label-Free Detection of Small Molecules", CSEM Scientific and Technical Report 2001, p. 54.

(Continued)

*Primary Examiner*—Christopher L. Chin
(74) *Attorney, Agent, or Firm*—William J. Tucker; Thomas R. Beall

(57) ABSTRACT

An evanescent-field sensor system and method of using the system to detect either liquid- or airborne biological pathogens, chemical agents, and other harmful or toxic species is provided. The sensor system involves 1) an evanescent-field sensor having a substrate surface with at least a partial bio- or chemo-responsive layer, which forms a part of a serially renewable sensing region; 2) an optical interrogation apparatus for monitoring the bio- or chemo-responsive layer; and 3) an air-fluid delivery system. The optical interrogation apparatus has a light source, an optical delivery system, and a detection instrument or device. The air-fluid delivery system includes either macro or micro-fluidic passages designed to convey biological or chemical analytes to a sensing region.

52 Claims, 16 Drawing Sheets

U.S. PATENT DOCUMENTS

| | | | |
|---|---|---|---|
| 6,242,267 B1 | 6/2001 | Herron et al. | 436/527 |
| 6,277,628 B1 | 8/2001 | Johann et al. | 435/287.2 |
| 6,455,004 B1 | 9/2002 | Tiefenthaler | 422/91 |
| 2002/0127565 A1 | 9/2002 | Cunningham et al. | 435/6 |
| 2002/0168295 A1 | 11/2002 | Cunningham et al. | 422/82.05 |
| 2003/0017580 A1 | 1/2003 | Cunningham et al. | 435/287.2 |
| 2003/0017581 A1 | 1/2003 | Li et al. | 435/287.2 |
| 2003/0026891 A1 | 2/2003 | Qiu et al. | 427/58 |
| 2003/0027327 A1 | 2/2003 | Cunningham et al. | 435/287.2 |
| 2003/0027328 A1 | 2/2003 | Cunningham et al. | 435/287.2 |
| 2003/0032039 A1 | 2/2003 | Cunningham et al. | 435/6 |
| 2003/0059855 A1 | 3/2003 | Cunningham et al. | 435/7.9 |
| 2003/0068657 A1 | 4/2003 | Lin et al. | 435/7.9 |
| 2003/0077380 A1 | 4/2003 | Lefkowitz et al. | 427/2.1 |
| 2003/0077660 A1 | 4/2003 | Pien et al. | 435/7.1 |
| 2003/0092075 A1 | 5/2003 | Pepper | 435/7.9 |
| 2003/0113766 A1 | 6/2003 | Pepper et al. | 435/6 |
| 2004/0132172 A1 | 7/2004 | Cunningham et al. | 435/287.2 |
| 2004/0132214 A1 | 7/2004 | Lin et al. | 436/518 |
| 2004/0151626 A1 | 8/2004 | Cunningham et al. | 422/58 |
| 2004/0223881 A1 | 11/2004 | Cunningham et al. | 422/82.05 |

FOREIGN PATENT DOCUMENTS

| | | |
|---|---|---|
| WO | WO 01/71316 | 9/2001 |
| WO | WO 01/71322 | 9/2001 |

OTHER PUBLICATIONS

R. Horváth et al., "Optical Waveguide Sensor for On-Line Monitoring of Bacteria", Optics Letters, Jul. 15, 2003, vol. 28, No. 14, pp. 1233-1235.

D. Stratis-Cullum et al., "A Miniature Biochip System for Detection of Aerosolized *Bacillus globigii* Spores", Anal. Chem. 2003, vol. 75, pp. 275-280.

M. Wiki et al., "Wavelength-interrogated optical sensor for biochemical applications", Optics Letters, vol. 25, No. 7, Apr. 1, 2000, pp. 463-465.

\* cited by examiner

FIG. 1

Sensing Medium

Evanescent Field

Optical Confinement Layer

Substrate

Input Probe Beam     Output Probe Beam

FIG. 2

Aerosol   ° ° ° ° °  ° ° Pathogens

Antibodies Y Y Y YY Y Y YYY YY  $n_c$

Waveguide  →$\beta_g$  $n_g$    $n_g > n_s > n_c$ $n_s$

Probe Light

FIG. 10

FIG. 15A  FIG. 15B  FIG. 15C
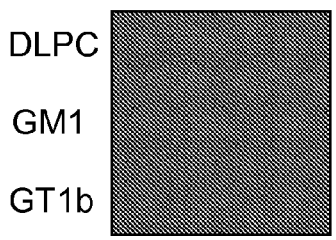
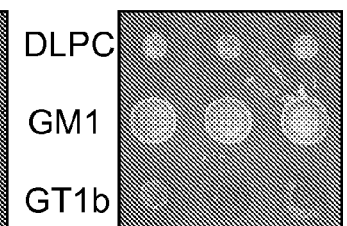
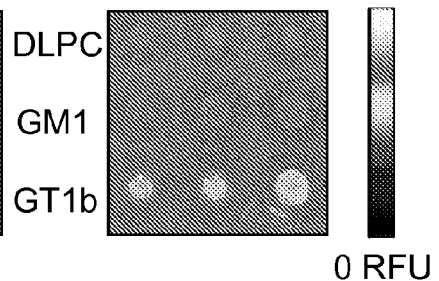
FIG. 15D
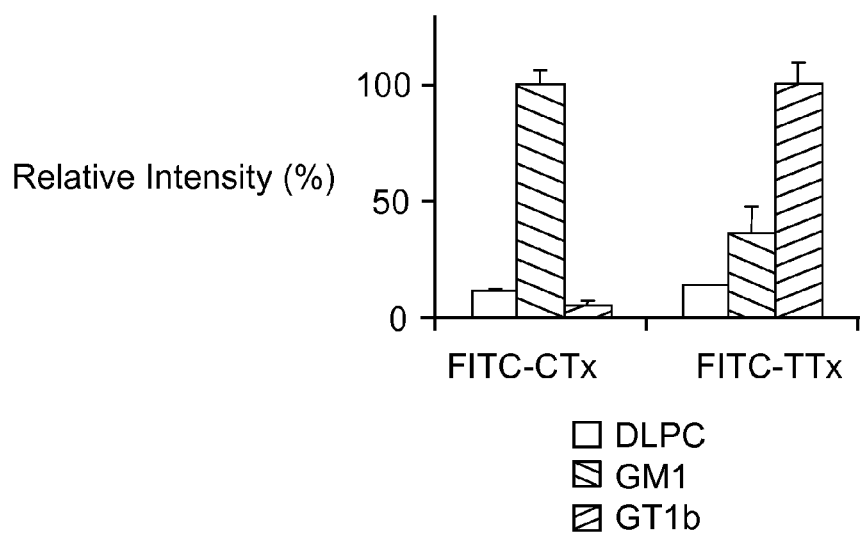

LABEL-FREE EVANESCENT-FIELD DETECTION OF BIOLOGICAL AND CHEMICAL AGENTS

CROSS REFERENCE TO RELATED APPLICATION

This application claims the benefit of U.S. Provisional Application No. 60/458,119 filed Mar. 27, 2003, the contents of which in its entirety is hereby incorporated by reference.

FIELD OF INVENTION

The present invention pertains to evanescent-field detection of biological and chemical agents. More particularly, the invention relates to a sensor system, its associated opto-electronic components, and methods of using the system to monitor real-time biological-binding events or chemical reactions for airborne or fluidic analytes.

BACKGROUND

Evanescent field-based sensors are fast becoming a technology of choice for accurate label-free detection of biological reactions. In recent years, the biological, pharmaceutical, and other research communities have begun to recognize that evanescent field-based sensors can be useful, high-throughput research tools to measure a variety of biological or biochemical functions. This technology typically involves the use of an optical evanescent field to sense changes in the local environment (refractive index) where a biological or chemical reaction takes place. A grating or prism can be used to couple light in and out of an optical mode, thereby probing the effective index of the mode, which changes together with the surface index. Changes in the angle or wavelength of the probe light, for example, indicate changes of the waveguide effective index that result from activity at the sensor surface. Evanescent field sensors have demonstrated high sensitivity, and an ability to detect binding reactions of as little as about 250 Da molecular weight (e.g., biotin binding to streptavidin). Typical spore-based pathogens (e.g., anthrax) are fairly massive ($\geq$20-50 kDa) entities compared to tiny pharmaceutical drug candidates that are the more traditional target of evanescent technology. As a result, such sensors and instruments should be sufficiently sensitive for airborne pathogen detection. Furthermore, because of their responsiveness to index of refraction, these kinds of sensors also respond to chemicals, and can therefore likewise detect chemical toxins.

SUMMARY OF THE INVENTION

The present invention, according to one aspect, relates in part to a sensor system for detecting either liquid- or airborne biological pathogens, chemical agents, and other harmful or toxic species. The sensor system comprises: 1) an evanescent-field sensor comprising a substrate surface having at least in-part a bio- or chemo-responsive layer, which forms a serially renewable sensing region; 2) an optical interrogation apparatus for monitoring the bio- or chemo-responsive layer, the optical interrogation apparatus comprising a light source, an optical delivery system, and a detection instrument; 3) an air-fluid delivery system, comprising either macro or micro-fluidic passages designed to convey biological or chemical analytes to one or more sensing regions. The substrate has reactant and non-reactant regions and can be modified with one or more materials, which enhance stable immobilization of the bio- or chemo-responsive layer. For instance, the bio- or chemo-reactive layer may include a pathogen-specific antibody or ganglioside probe for biological analytes. Alternatively, the bio- or chemo-reactive layer may be designed to adsorb a chemical molecule or moiety of interest, resulting in either a change in mass or refractive index. The change in mass may result from the adherence of the chemical molecule to the surface or a removal of the original chemistry from the sensor surface.

The evanescent-field sensor, according to the invention, has a continuous substrate having thereon at least one, preferably two, or more contiguous sets of either sensor regions or arrays of sensors, wherein each array comprises a predetermined set of multiple regions for biological or chemical sensing. The bio- or chemo-responsive layer in a sensing region is specifically formulated to react with particular biological or chemical analytes. In preferred embodiments, the evanescent-field sensor includes a collection of individual substrates, each having one or more sensing regions that can be optically interrogated either in series or in parallel. Preferably, the substrate is optically transparent. The system preferably also includes a sample collection or concentration unit to concentrate in situ particles in the air before they are drawn into the sensing region.

The sensor system, according to an embodiment, preferably includes a substrate with tensile strength and pliability can be supplied from a dispensing device as a single unit in a continuous fashion; and the substrate is configurable to a fraction of its fully extended length along its longest dimension without breaking, and can be retrieved from such configuration as a continuous body suitable for performing molecular interactive assays with toxin targets. Alternatively, the evanescent-field sensor has a substrate in the form of a revolving platform. According to certain embodiments, the device comprises a collection of individual substrates, each having one or more sensing regions that can be optically interrogated in series.

In another aspect, the present invention pertains to a method for detecting toxins. The method comprises: providing an evanescent-field sensor system like that described above, having at least in-part a bio- or chemo-responsive layer that forms a serially renewable sensing region; exposing an individual sensor array to an environment with unknown hazardous contaminants; and monitoring a response from said sensor system to determine a contamination level. The sensor system may be deployed on a mobile platform, which can be moved to or through the contaminated environment. Sensor response signals can be transmitted to a remote analysis location.

Additional features and advantageous of the present invention will be revealed in the following detailed description. Both the foregoing summary and the following detailed description and examples are merely representative of the invention, and are intended to provide an overview for understanding the invention as claimed.

BRIEF DESCRIPTION OF THE DRAWINGS

FIG. 1 is a schematic representation of a generic evanescent-field sensor.

FIG. 2 is a schematic representation of aerosol pathogen flowing over a Grating-coupled Waveguide (GCW) sensor and being detected by the sensor.

FIG. 10 shows an embodiment of the present invention, wherein the substrate of the sensing system is a film.

FIG. 15 shows toxin binding to ganglioside probes: A) control, B) cholera, and C) tetanus.

DETAILED DESCRIPTION OF THE INVENTION

Section I—Definitions

Figure 3A:
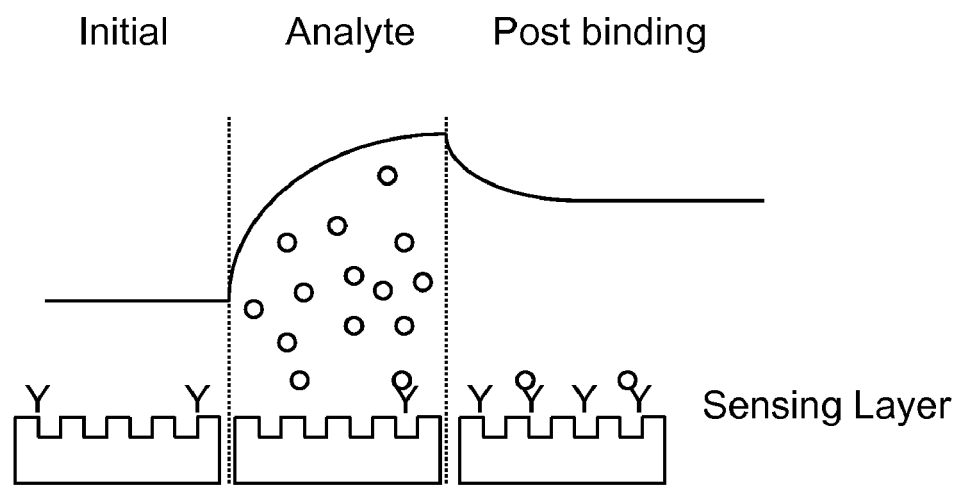
FIG. 3A is a schematic representation of a GCW structure having on its surface bio- or chemo-responsive probes, and depicts changes, over three-stages, in monitored signal response as the evanescent-field sensor surface encounters different analytes. Initially, the response is at a baseline level. As analytes are passed over the surface, some particles bind with an associated increase in signal. The post-binding signal response is higher than the baseline.
Figure 3B:
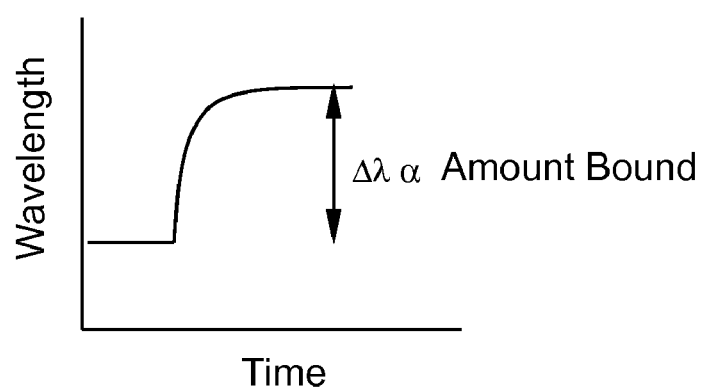
FIG. 3B is a representation of the change in wavelength ($\Delta\lambda$) of the outgoing light beam, which is proportionate to the amount of analyte bound.

Before describing the present invention in detail, this invention is not necessarily limited to specific compositions, reagents, process steps, or equipment, as such may vary. As used in this specification and the appended claims, the singular forms "a," "an," and "the" include plural referents unless the context clearly dictates otherwise. It is also to be understood that the terminology used herein is for the purpose of describing particular embodiments only, and is not intended to be limiting. All technical and scientific terms used herein have the usual meaning conventionally understood by persons skilled in the art to which this invention pertains, unless context defines otherwise.

The term "air-fluid delivery system" as used herein refers to a fluidic (i.e., gaseous or liquid) system that can collect samples of biological or chemical analytes from the atmosphere or surrounding environs, and deliver the samples to a sensor.

The term "analyte," "toxin," or "target" as used herein refers to biological pathogens, chemical agents, and other harmful or toxic species to be detected.

The term "bio-responsive" or "chemo-responsive" as used herein refers to the ability to adsorb, desorb, react with, or bind a biological or chemical species.

The term "bio- or chemo-responsive layer" as used herein refers to a collection of probes on a substrate surface of an evanescent-field sensor.

The term "evanescent" as used herein refers to that portion of an optical field where the effective index of the optical field exceeds the local index of the medium, thereby necessitating an exponentially decaying field in space, according to Maxwell's Equations.

The term "evanescent-field sensor" as used herein refers generally to any kind of sensor where an evanescent optical field interacts with a medium to be sensed, and changes in the optical field can be detected to indicate properties or changing characteristics of the medium.

The term "microspot" as used herein refers to a discrete or defined area, locus, or spot on the surface of a substrate, containing probe material. One or more micropots, as in an array, constitute a sensing region.

The term "probe" as used herein refers to either a natural or synthetic, bio- or chemo-reactive molecule, which has been immobilized to a substrate surface constituting part of a sensing medium. A set of probes can bind or otherwise react with analytes. Examples of probes which may be employed according to this invention may include, but are not limited to, antibodies, (e.g., monoclonal antibodies and antisera reactive with specific antigenic determinants), glycolipids including gangliosides, pharamaceutical or toxin molecules, polynucleotides, peptide nucleic acid (PNA), peptides, proteins, cofactors, lectins, polysaccharides, viruses, cells, cellular or lipid membranes, membrane immuno-receptors, and organelles. For chemical detection, the probes may include a polymer matrix, or a ligand-gated ion channel membrane. Preferably, probes are arranged in a spatially addressable manner to form an array of microspots. When the array is exposed to a sample of interest, molecules in the sample selectively and specifically binds to their binding partners (i.e., probes). The binding of a "target" to the probes occurs to an extent determined by the concentration of that "target" molecule and its affinity for a particular probe.

As used herein, the term "receptor" refers to a molecule that has an affinity for a ligand. Receptors may be naturally-occurring or man-made molecules. They may be employed in their unaltered state or as aggregates with other species. Receptors are sometimes referred to in the art as anti-ligands. A "ligand-receptor pair" is formed when two molecules have combined through molecular recognition to form a complex.

The term "sensing region" as used herein refers to an area or window on a surface of an evanescent-field sensor where analytes may attach and be detected. Over the total surface of an evanescent-field sensor, there is at least one, preferably a plurality of sensing regions that may be each optically accessed in sequence or in parallel. In other words, a sensing region is analogous to a slide or a frame of film.

The term "substrate" or "substrate surface" as used herein refers to a solid or semi-solid material, which can form a stable support and is capable of functioning as an evanescent-field sensor. The substrate surface can be selected from a variety of materials.

Section II—Description

The present invention pertains, in part, to a sensor system and method for detecting toxins by means of evanescent-field optics. FIG. 1 is a schematic representation of a generic evanescent-field sensor device. An optical confinement layer, such as a waveguide, provides a zone through which an optical mode propagates. A waveguide offers good sensitivity to the surrounding environment or medium (index). The light source provides the evanescent optical field that penetrates into a medium to be sensed. Because this evanescent field extends into the medium, changes in the mass or refractive index of the sensing medium cause changes in the properties of the field in the optical confinement layer. As the sensor surface encounters different biological or chemical molecules, the evanescent field registers changes in response, which can be monitored. An incident or input probe light beam is used to interact with the confined optical energy, and an output light beam subsequently contains the desired information. This information is typically in the form of either a change in the wavelength or angle of the output light, since interaction between the confined optical mode and the probe beam requires precise matching of the wavelength and/or angle parameters as dictated by the refraction/diffraction physics employed in either the prism, grating, dielectric stack, or etc. to extract information from the sensor.

According to a second aspect of the invention, the method of using the evanescent-field sensors described above to detect various kinds of species comprises: providing a sensor system having an evanescent-field sensor comprising a substrate surface having at least in-part a bio- or chemo-responsive layer, which forms a serially renewable sensing region, and a continuous substrate having thereon at least two or more contiguous sets of sensor arrays, wherein each array comprises a predetermined set of multiple regions for biological or chemical sensing. An individual sensing region or sensor array may be exposed an environment with unknown hazardous contaminants; and monitoring a response from said sensor system to determine a contamination level.

A. The Sensor

According to the invention, the sensor system provides a multiplexed, high-throughput format for evanescent detection of biological entities, chemical agents, and other harmful pathogenic or toxic species. The sensor system comprises an evanescent-field sensor having a bio- or chemo-responsive layer, which forms part of a sensing region, on at least part of a substrate surface. Each sensing region provides an area or window in which analyte-binding sites, or microspots, on the substrate can be optically interrogated.

In order to render the sensors active for pathogen or toxin detection, either the entire continuous substrate surface or at least parts thereof would be coated with an appropriate biological or chemical species for the desired bio- or chemo-reactivity. In other words, coating the entire substrate with a chemo- or bio-reactive substance is not generally required; only the active microspots of a sensor area need to have a reactive coating. In the instance of multiplexed sensing, each row of separate sensors (along the continuous direction of the substrate) may be distinguished by a different bio- or chemo-reactive coating. In addition, one may also include a control sensor with each array of multiplexed toxin sensors where no reactive coating is employed, in order to distinguish true specific detection from non-specific (background) noise.

The sensing medium on the substrate is a bio- or chemo-reactive layer comprising a variety of ligands or receptor molecules, referred to as probes, which can bind with specificity to fluid- or airborne analytes. To develop a sensor specific to pathogens or toxins probes need to be inmuobilized securely on the surface of the sensor. The surface chemistry in or around a sensing region of the substrate is usually tailored for immobilizing particular kinds of probes. The substrate may comprise at least a binding entity selected from either a biological or chemical molecule, each having a specific affinity for another molecule through either covalent or non-covalent bonding. Preferably, a specific binding entity may contain (either by nature or by modification) a functional chemical group (primary amine, sulfhydryl, aldehyde, carboxylic, acrylic, etc.), a common sequence (nucleic acids, an epitope (anitbodies), a hapten, or a ligand, that allows the binding entity to bond or react covalently or non-covalently with a common function group on the surface of the substrate. Specific binding entities include, but are not limited to: deoxyribonucleic acids (DNA), ribonucleic acids (RNA), synthetic oligonucleoides, antibodies, proteins, peptides, lectins, modified polysaccarides, synthetic composite macromolecules, functionalized nanostructures, synthetic polymers, modified/blocked nucleotides/nucelosides, modified/blocked amino acids, fluorophores, chromophores, ligands, chelates, and haptens. In multiplexed embodiments, each microspot within an array of the sensor may have a different bio- or chemo-responsive layer specifically formulated to react with a particular biological or chemical analyte/target. For some embodiments, a further biological preparation of the surface may include applying non-specific binding blocking agents, etc.

One requirement for high-specificity identification of pathogens is the availability of probes (e.g., antibodies, proteins, immuno-receptors, etc.) that show a large binding affinity for the target. Often, antibodies specific to a pathogen are utilized, since they provide a high degree of specificity. The probe may be selected according to their specificity for certain functionalism. For example, the probes may include antibodies against various different surface-marker molecules of a particular pathogen, such as the four or five different antibodies that can bind with these kinds of functionality of anthrax. Sometimes, however, production of such materials is often difficult. For instance, antibodies may be hard to produce and purify, and a different probe must be substituted. Other examples of pathogen targets that are more available and just as specific in their capture of pathogens as antibodies may include gangliosides, which are sugar/lipid complexes targeted by many toxins (including anthrax).

Recently, immobilization of gangliosides on surfaces for binding assays have been demonstrated (Fang et al., "Ganglioside Microarrays for Toxin Detection," Langmuir 2003, 19, 1500-1505). Details for detecting toxins using an array of biological membrane are also provided in U.S. Provisional Patent Application No. 60/392,275, which is incorporated herein by reference. For binding assays, gangliosides can be immobilized on surfaces of an evanescent sensor prior to deployment of the sensor. As an added bonus, the use of such binding reactions can result in greater specificity (fewer false positives) than most absorption spectrum-based standoff detection techniques. Alternatively, the sensing or responsive layer may include a polymer matrix, biomembranes with a ligand-gated ion channel, or chemical compounds may be used for detecting chemical toxins.

Once the sensor surface is prepared, the sensor is essentially ready for airborne pathogen detection, as shown in FIG. 2. FIG. 2 depicts one of a possible plurality of sensing regions located across the substrate surface of a sensor. When in operation, a sensing region is exposed to a sample of air or fluid at a time. The sensor responds when the airborne pathogen or toxins bind to the probes, allowing the detection of this change in the effective index at the sensor surface as described above. Particles for which the responsive layer is designed will bind with specificity. Non-specific binding of other particles, however, will also occur and cause the sensing region to become contaminated over time. Once the sensing region becomes contaminated the optical interrogations tends to become less accurate. Being mindful of this, the sensor system is designed according to the invention, such that each evanescent sensor has a serially renewable sensing region. That is, a plurality of sensing regions located on the surface of a substrate. A fresh sensing region can be exposed for binding and interrogation after a predetermined interval of time once the former sensing region reaches a certain level of non-specific contamination. Often the specific time period may depend on specific enviromnental factors or conditions, such as pollution level or aerosol concentrations.

The sensor system according to the present invention can exhibit improved degrees of sensitivity and specificity. According to the invention, the sensor is able to detect the presence of microbes (e.g., virus or bacteria) in a sample at levels of at least about 1 organism per liter, biological toxins present in a sample at levels of at least about 1 or 10 femtomoles per liter, and chemical toxins at levels of about 50-100 attomoles per liter. Furthermore, these reactions can be monitored in real-time, permitting their use in unmanned aerial vehicles, mobile equipment on the ground, and locality- or community-wide response networks.

Evanescent-field sensing generally monitors a change in optical phase. Numerous optical devices incorporate phase detection. Some of examples of these may include a resonant ring, a Mach Zehnder interferometer, or a Hartman interferometer. The sensor may take a variety of other forms, including a patterned optical circuit. The sensor, according to certain embodiments, is a waveguiding structure formed by a waveguiding containment layer, film, or effective index region located over or against a substrate. Preferably, the waveguiding region has a refractive index of at least 0.1% higher than the refractive index of the substrate. A diffraction grating may be contained in the waveguiding structure. A bio- or chemo-responsive layer is deposited adjacent to the waveguiding body or film, wherein the bio- or chemo-responsive layer is capable of interacting with the toxins of interest. The sensor may be fashioned from a substrate coated with a metallic film capable of supporting surface plasmon modes. In another embodiment, the sensor may be a substrate coated with multiple dielectric layers. The dielectric layers have varying optical indices, and the optical field has an evanescent tail extending beyond the layer immediately in contact with a medium to be sensed.

B. System Design

The basic sensor system is fairly simple to understand. Evanescent-field sensors can be made in a variety of shapes and sizes, and with a variety of materials, including glass, dielectric materials, metals, metal oxides, as well as relatively inexpensive plastics. Ideally, many sensors should be packaged together to provide the ability to switch to new sensors as old ones become contaminated or the surface chemistry is rendered inactive through use. In view of these considerations, the present invention provides a continuously renewable substrate that incorporates numerous sensors. The optical monitoring beams would presumably interact with only a subset of all of microspots on the sensor substrate at any given time.

No practical embodiment of toxin sensing technology, however, would target only one specific toxin. For this reason, multiple sensors should be operable in a multiplexed format. This could involve simultaneous monitoring of a plurality of sensors, or simply a sequential detection of individual sensors. In order to accommodate multiplexing, the continuous substrate would preferably have groups of sensors arranged in which the number of sensors in each group is roughly equal or corresponds to the number of toxin species one would wish to detect. For instance, if one wishes to monitor five toxin species, the substrate may be configured to contain five (5) adjacent evanescent field sensors. If each sensor is in the form of a microspot of about 2 mm in diameter, for example, a resulting array of microspot sensors would be roughly 10 mm wide×2 mm long, repeated many times along the entire length of the continuous substrate. Alternatively, if spatial considerations do not permit placement of the desired number of multiplexed sensors in a single line on the substrate, one could organize arrays of sensors in groupings of a two-dimensional rectilinear matrix, with two or more parallel rows and columns. For example with respect to microspots of 2 mm in diameter, like above, on a 10-mm wide substrate, 15 different toxins could be monitored with a 3×5 array of microspot sensors.

According to certain embodiments of the system, the evanescent-field sensor may have a collection of substrates, each having one or more sensing regions that can be optically interrogated in series or in parallel. In an embodiment, the evanescent-field sensor has a continuous substrate with at least two or more contiguous sets of sensor arrays on the substrate surface, such that each array comprises a predetermined set of multiple regions for biological or chemical sensing. In each array of sensors, the bio- or chemo-responsive layers are specifically formulated to react with one or more particular biological or chemical analyte. The substrate has tensile strength and pliability and can be supplied from a dispensing device as a single unit in a continuous fashion. The substrate can be configured to a fraction of its fully extended length along its longest dimension without breaking, and can be retrieved from such configuration as a continuous body suitable for performing molecular interactive assays with said molecular targets. For instance, the substrate is an optically transparent (polymer) film of about 50 microns to about 2 mm thick. In other embodiments, discussed in detail below, the evanescent-field sensor may also take the form of a rotatable platform.

Figure 4A:
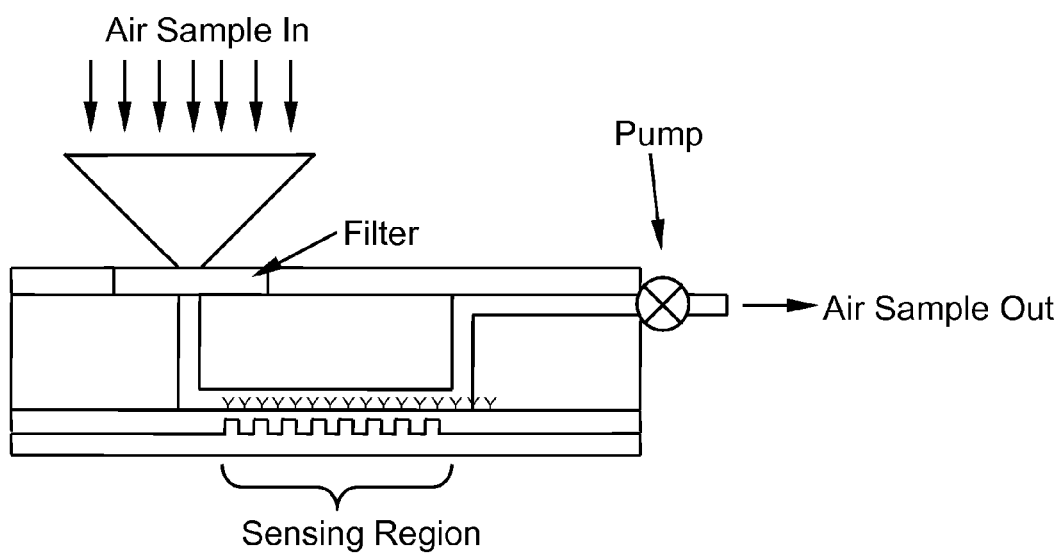
FIG. 4A is a schematic representation of an air-fluidic delivery system according to the present invention.
Figure 4B:
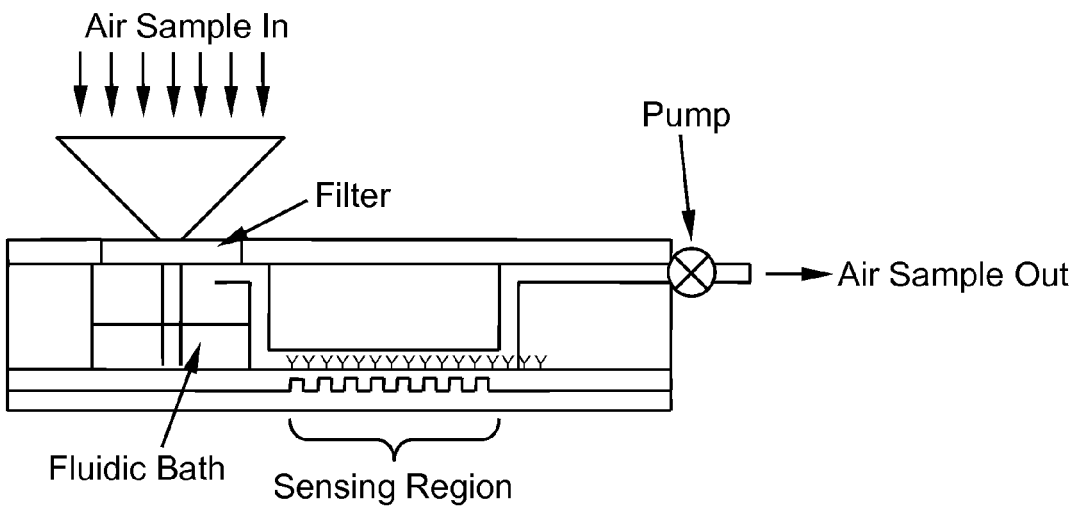
FIG. 4B is an alternate is a schematic representation of an air-fluidic delivery system.
Figure 5:
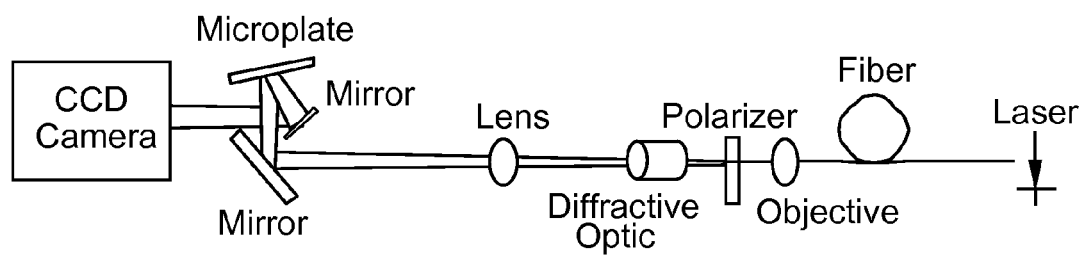
FIG. 5 is a schematic representation of a multiplexed angular sensor system design.
Figure 6A:
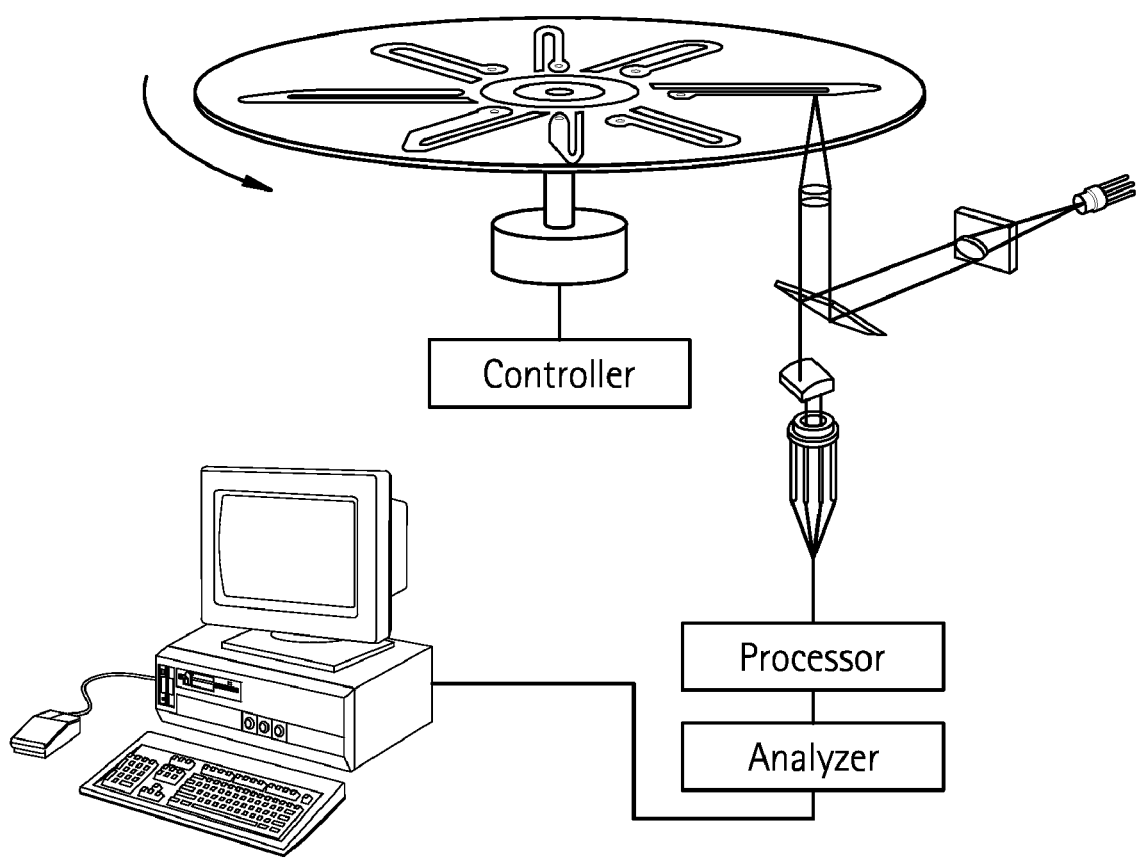
FIG. 6A is an alternate schematic representation of a sensor system design.
Figure 6B:
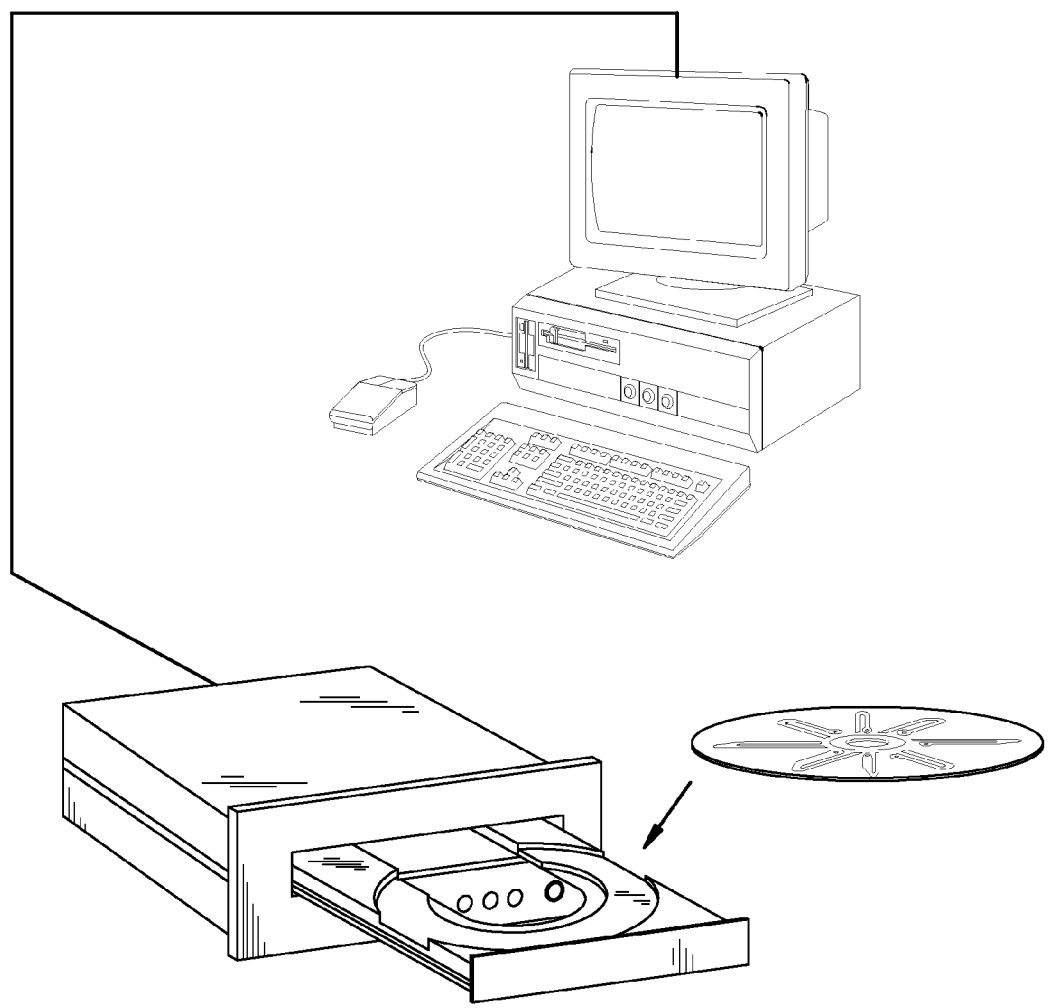
FIG. 6B is a variation of the system design shown in FIG. 6A.

The pathogen can be introduced to the sensor in a variety of ways, including direct air flow as well as fluid capture/flow. Hence, fluid (gas, aerosol, or liquid) flow across the sensor is another component of any sensing system. Fluids could be introduced either with macro or micro-fluidic systems, and incorporate reagents for assays included in the instrument. An air sample delivery system may include air filtration systems combined with flow channels, monitors, or even pathogen concentrating technology. An embodiment may have a network of channels made up of a number of different macro or microstructures, which may encourage efficient mixing of an air sample or vary the velocity of air sample flow by changing the dimensions of the channels. FIG. 4A, depicts a schematic representation of typical embodiment of a delivery system. The air-fluid delivery system may include, but is not limited to, a funnel-shaped air sample collector, a replaceable filter, a network of macro or microchannels or passages, and a fan, air handler, or pump to draw air or liquid through the passages. Moreover, airborne pathogens could even be delivered via a hybrid air/fluid system. Several systems exist commercially to capture airborne targets in a fluid. Moreover, a unit may be incorporated to concentrate analyte or toxin particles per unit of air sample in situ, before the particles are flowed into the sensing region. Examples of such a unit, as illustrated in an embodiment of FIG. 4B, may include a liquid bath, such that after passing through the filter, the air sample is injected into the liquid bath before passing the sensing region while suspended in fluid.

In other embodiments, the air sample outlet may be redirected temporarily back through the sensing region to enable potential continuous circulation of the same air sample for a certain prescribed period of time before the sample is discharged from the system. This may allow better sampling of the contents in the air. The entire sensor system may be engineered to fit within a compact, mobile housing design.

An embodiment for a replaceable filter may be in the form of a replaceable cartridge. A cartridge design also has the advantage of being configurable to specific uses, such that different filter sizes can be implemented depending on the desired application. In the cartridge, the filter may be wound into a continuous roll. Analogous to the sensing regions on a sensor substrate, after certain period of time or when it become necessary, the filter roll can be mechanically advanced forward a fixed length to expose a new filter surface. A continuous roll of filters, limited only by the size of the filter roll and level of contamination present in the local environment, can provide a more efficient filtration process. Hence, the instrument can be deployed in the field for a longer interval of time without the need to change the filter or provide other maintenance.

One of the most important components of the sensor system is an optical interrogation apparatus for monitoring said chemo-responsive layer. The sensor is monitored by an optical beam, as shown in either FIGS. 2 or 7B, where the angle and/or wavelength of the incoming light are specifically selected to excite and probe the (guided mode) evanescent field. The optical instrumentation therefore includes of a light source, an optical delivery system (typically free-space or fiber), and a detection instrument. The light source may be either white light or of a single wavelength, as from a laser, and other delivery devices may be employed, such as an optical fiber. The optical delivery system may include a diffraction grating, a prism, or a specifically tailored dielectric stack in order to couple incoming and outgoing optical probe beams to an evanescent sensing field. According to some embodiments, the optical delivery system may employ a diffractive optic to generate multiple optical probe beams for multiplexed monitoring of multiple sensing regions. The optical delivery system may utilize optical fiber to deliver or collect a light signal from the sensors. An optical detector may be, for example, a photosensitive array, a CCD camera, or some other instrument or means that can sense a change in either the wavelength or angle of an out-going light beam.

FIG. 5 represents an example of an instrument used to interrogate a GCW evanescent sensor. The basis of multiplexing is a diffractive optic that generates a 19×19 array of beams, and the lens places these beams on each well of an arrayed sensor substrate.

This geometry demonstrates the ability to utilize a diffractive optic to multiplex several sensors without many additional optics. Data relating to detection of biological or chemical targets obtained with this instrument is detailed below.

Other designs for the system are depicted as schematic representations in FIGS. 6A and 6B. For illustrative purposes, an embodiment with a rotating sensor substrate is shown being optically interrogated with a light source, like a laser. A detector captures the optical response signal, and may be connected remotely or proximally to a processor and/or analyzer device, such as a computer, which can provide data and feedback to a person monitoring the sensor.

Section III—Examples of Embodiments

Having described the general concept of the present invention, the following describes examples of possible embodiment. These detailed examples, however, are only some of the many possibilities for a sensor substrate design according to the present invention.

A. Grating Coupled Waveguide (GCW) Sensor

GCW sensors are excellent examples of evanescent field technology. While some features may be unique to GCW devices, this invention pertains to any evanescent-based biological sensors, where an evanescent optical field responds to biological events. Therefore, the sensor could have a transparent optical waveguide with grating or prism coupling (as above), metallic layers that exhibit surface plasmon modes, or even dielectric stacks that confine the optical field with total internal reflection. In any case, the general embodiment involves the monitoring of the optical mode as its evanescent tail responds to the biological stimulus. Optical sensor for selective detection of substances and/or for the detection of refractive index changes in gaseous, liquid, solid and porous samples. One may gain a fuller understand of specific details of the present invention in examples of similar GCW sensor devices, such as described in U.S. Pat. Nos. 4,815,843, 5,071,248, 5,738,825, or 6,455,004, to Tiefenthaler, et al., the contents of which are incorporated herein by reference.

FIG. 7A depicts a generic schematic representation of a GCW sensor device. A waveguiding film and thin grating sit against a thick substrate—the order of the waveguiding film and thin grating may be interchanged or reversed. Furthermore, the waveguide need not be a continuous single film, but also could be formed with various materials and geometries causing an effective index-guiding region. Likewise, certain applications may require the addition of a very thin layer of surface chemistry to assist in toxin binding, adsorption, or desorption. According to an embodiment as depicted in FIG. 7B, the biological medium serves as the superstrate (cover layer) in contact with the GCW sensor.

An example of a GCW design may involve a plastic substrate, where the substrate index $n_s=1.53$, the grating pitch $\Lambda=538$ nm, the grating thickness is $t_g=10$ nm, the waveguide index $n_f=2.01$, the waveguide thickness $t_f=110$ nm, and the superstrate index is nominally the index of water (the solvent in which most experiments are performed, $n_c \geqq 1.33$). These numbers are of course only nominal values, since larger ranges of these parameters still satisfy the requirements for proper sensing operation. For instance, the grating pitch can range from about 300 nm to 5000 nm or more, depending upon the desired wavelength of operation and target device sensitivity. The substrate and waveguide indices can range from about 1.0 (air) to about 3.5 or greater depending upon the materials chosen. In order to provide optical confinement however, the substrate index is usually lower than the index of the confinement layer. The waveguide thickness is typically less than the operating wavelength in order to maintain a single confined mode for sensing.

Figure 7A:
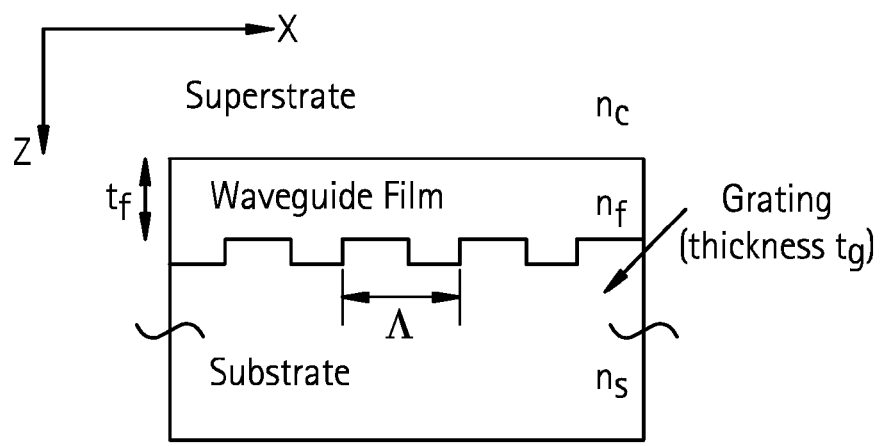
FIG. 7A is a schematic representation of a typical Grating-coupled Waveguide (GCW) Device.
Figure 7B:
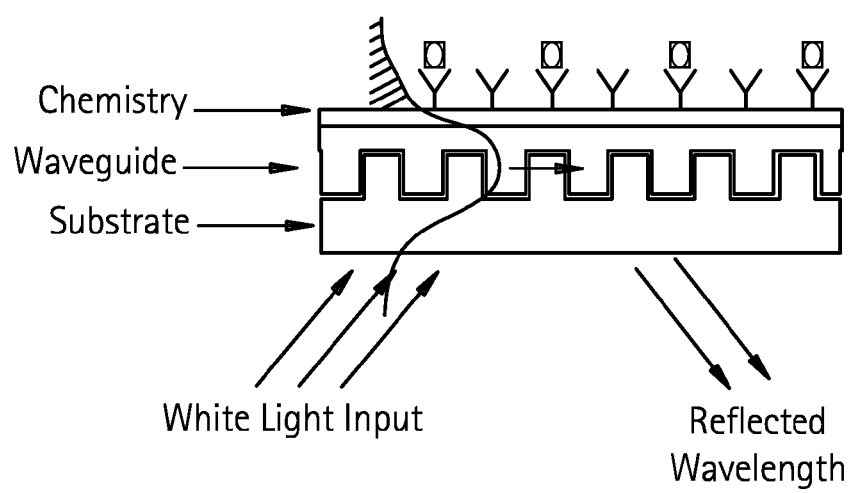
FIG. 7B is a schematic representation of detection using GCW device.

The physical operation of GCW devices can be understood as an interaction between a free-space light field and the device's waveguide modes. This interaction is made possible by the diffraction grating, designed to diffract light of specific wavelengths at specific angles to their incoming propagation vectors. In a GCW device, like in FIG. 7B, a particular wavelength incident at a particular angle will diffract directly into the fundamental mode of the waveguide, and propagate for some (short) distance. The coupling between grating and waveguide preserves momentum, and detailed mathematics can be found in the literature; for brevity, we will simply mention that the difference in the real part of the x-propagation coefficient between the free-space and waveguide mode will equal the wave vector of the grating. In other words, $$\beta_g - \beta_x = \frac{2\pi}{\Lambda} \quad (1)$$

where $\beta_g$ is the waveguide propagation constant, $\beta_x$ is the free-space propagation constant, and $\Lambda$ is the grating period. The same grating that couples this particular wavelength into the grating will also serve to couple this light back out of the waveguide, according to the same diffraction angle laws that governed the input coupling. The net result is the angular redirection of a narrow wavelength band of light incident on the GCW device; this narrow-band response is often referred to as a Wood anomaly. The design of the device determines the input angle and wavelength for waveguide coupling, as well as the output angle. This type of functionality is analogous to directional optical filtration, with obvious applications wherever optical filters are needed.

Figure 8:
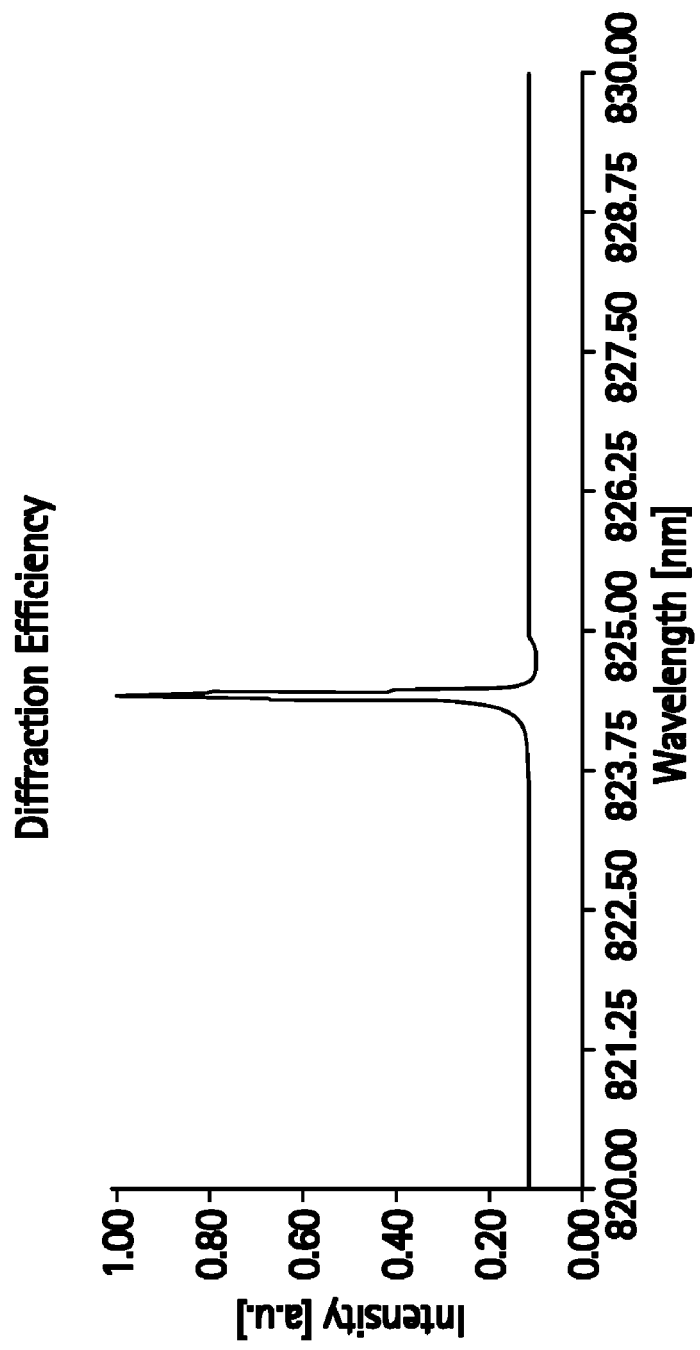
FIG. 8 shows the reflection anomaly in the GCW structure illustrated in FIG. 7A.

To maintain simplicity and efficiency of operation, the devices employed for biosensing are usually designed such that only the zeroth diffracted orders of the grating propagate in free space. The higher diffraction orders are avoided by designing a sub-wavelength grating, i.e., grating pitch is smaller than the desired operating wavelength. In such a situation, the coupling efficiency between the input/output light and the waveguide mode is large since higher orders do not remove power from the system. Moreover, since only the zeroth reflected and transmitted beams exist in free space, the GCW can thereby produce nearly total reflection or transmission of the desired (anomalous) wavelength. FIG. 8, below shows a GSOLVER (rigorous coupled-wave analysis, or RCWA code) analysis of the structure of FIG. 7A, when the input light angle is 3°. The resonantly reflected beam (at 3° from the normal) occurs in the vicinity of 824 nm for incident TE light, and a cover index of 1.33 (water).

Figure 9:
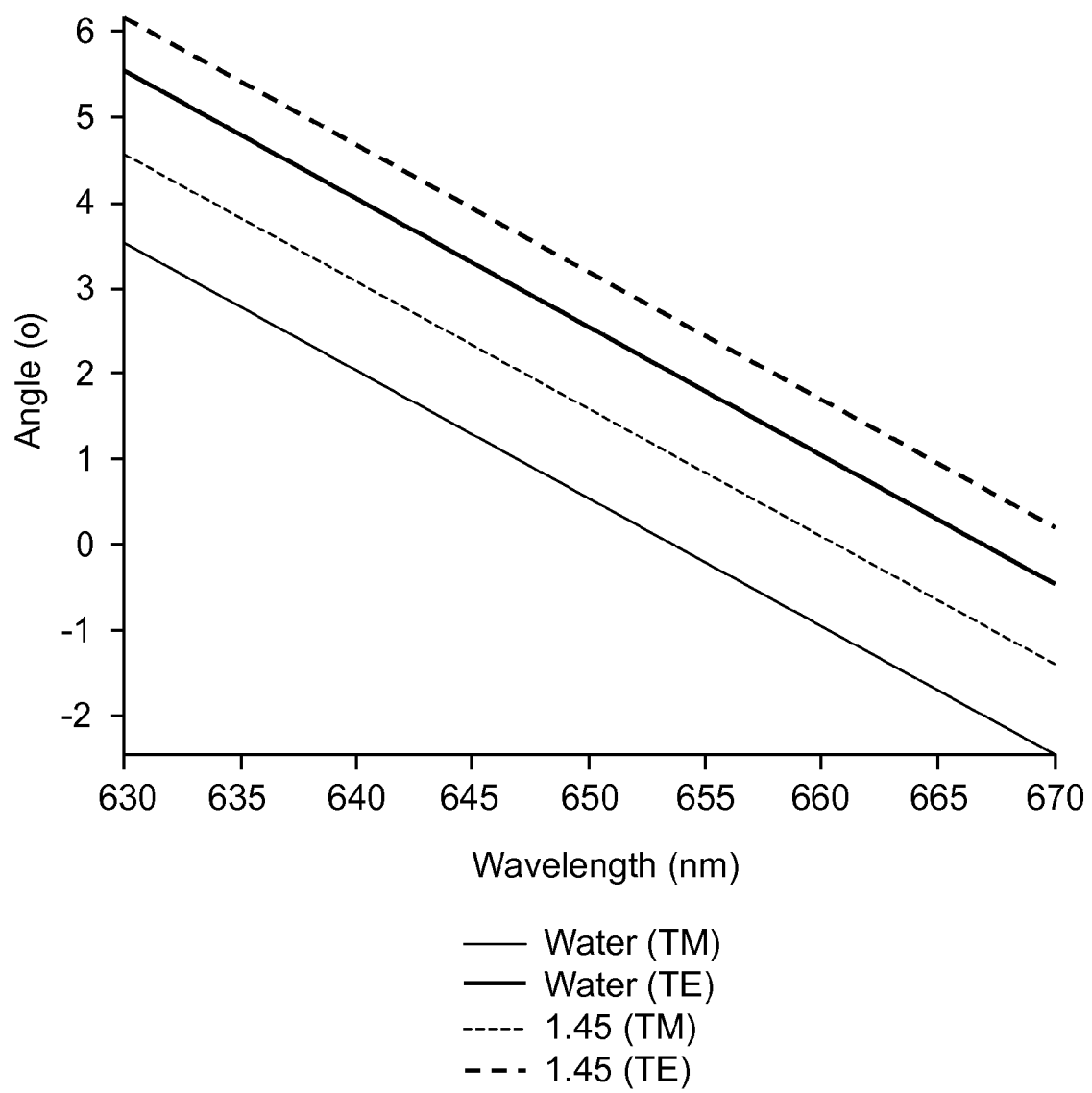
FIG. 9 is a plot of the theoretical angle vs. wavelength curves for a GCW sensor.
Figure 11A:
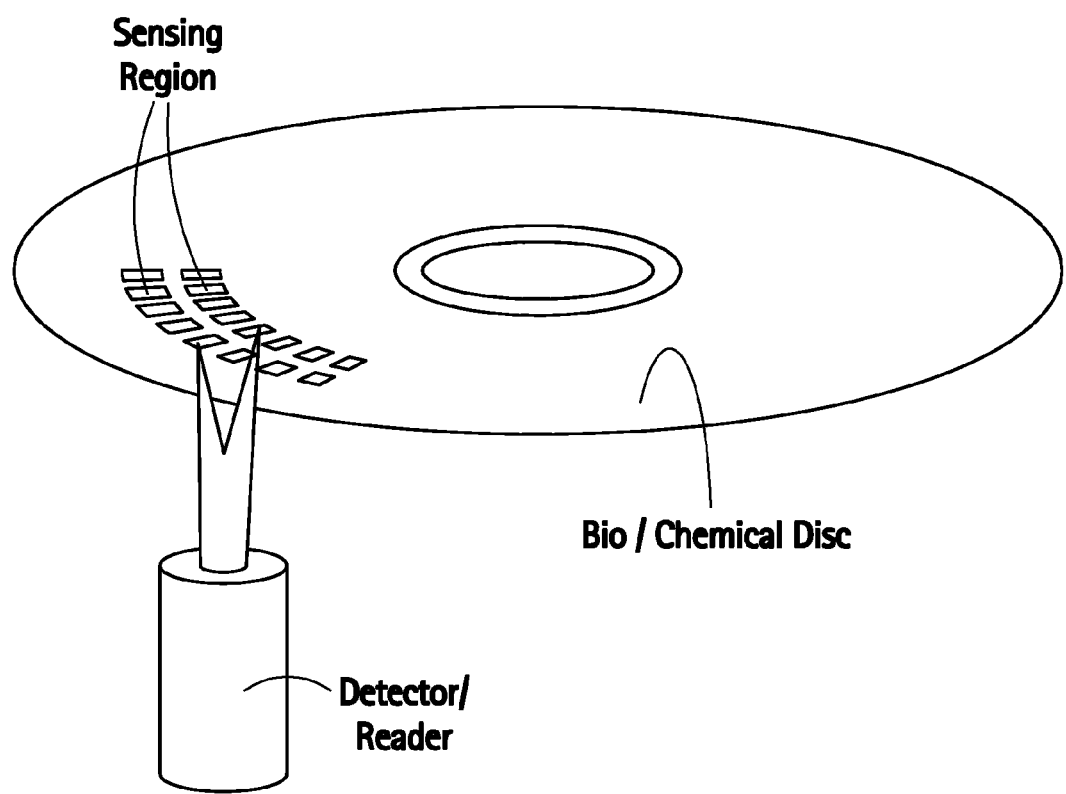
FIGS. 11A-D depict variations of an embodiment of the present invention, in which multiple sensing regions are located on a rotatable substrate or platform.
Figure 11B:
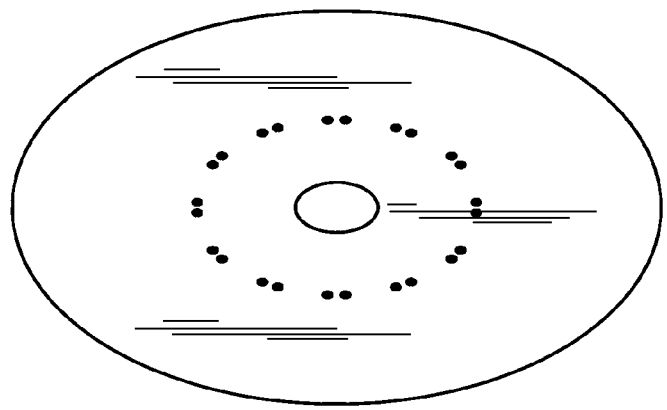
Figure 11C:
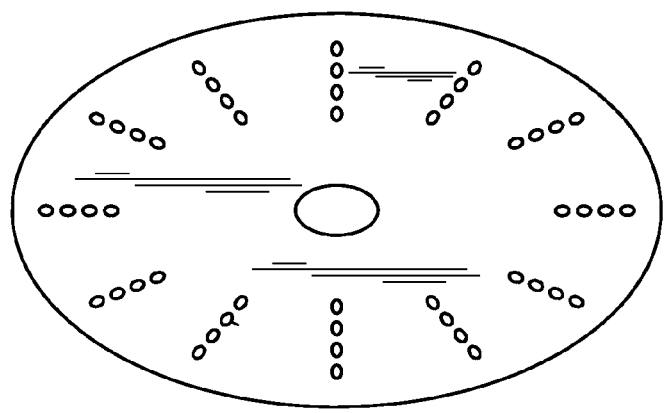
Figure 11D:
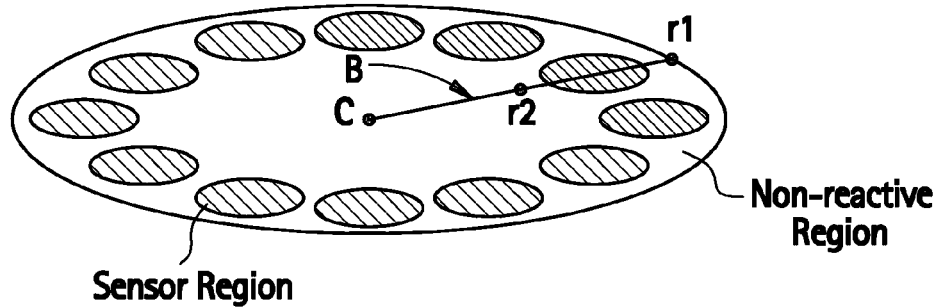

An ability to tune the location (in both wavelength and angle) of the above resonance with the index of refraction of the waveguide superstrate has led to the use of GCW devices for biosensing applications. The evanescent tail of the propagating waveguide mode senses the superstrate index changes, thereby altering the guided mode's effective index. This changes the resonance condition of the GCW according to equation (1) above, and the resonance thus shifts to a new wavelength or angle location. The relationship between angle and wavelength is displayed in FIG. 9 for a particular commercial sensor. The different curves show behavior for both TE and TM polarizations for two different cover indices (water index =1.333).

B. Film-Based Substrates

The availability of small-volume sensors allows novel designs for compact, renewable biological pathogen or toxin systems. Individual polymeric sensors may be fabricated on flexible substrate. A portion of the substrate, having two arbitrarily designated ends, may be bent along its longest dimension into an arc or sinusoidal configuration, wherein one end touches or nearly touches the other, without breaking or inflicting irrevocable physical damage to the substrate. For instance, an individual sensor substrate may be made to measure 9 mm$^2$×1 mm thick. Polymeric films of about 50 μm to about 1 or 2 mm thickness could instead be made, reducing the total sensor volume to only 1.35 mm$^3$. This technology is ideally suited for military or civil defense and security applications, where miniaturization and mobility are critical concerns.

In particular embodiments, polymer film-based GCW sensors could be made compatible with mechanized commercial 35-mm film. Such a solution can take advantage of immediately available commercial technology from the film industry. For instance, a sensing region, according to such an embodiment, may be thought of as being analogous or equivalent to the surface of a frame of film. Film reels, sprockets, drive motors and other devices or mechanics of cameras or motion picture projectors can be adapted to advance each sensing region like a frame of film. Moreover, this approach would produce a renewable sensor surface, where a continuous roll provides new sensors that advance when the prior sensing surface is spent.

Figure 10:
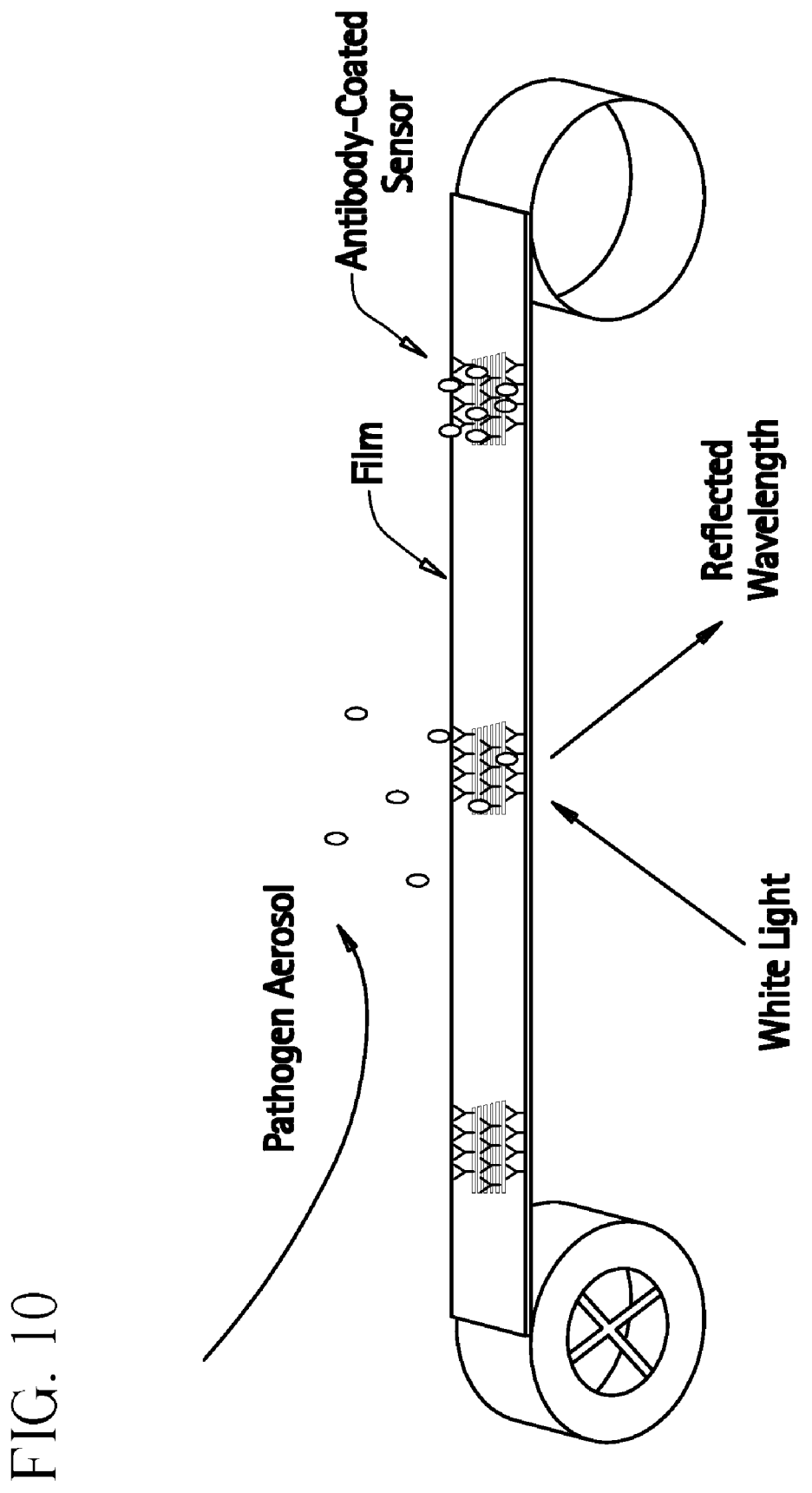

As an example, films of about 50-150 or 200 μm thick with embedded GCW sensors may be wound into a continuous roll. This embodiment is depicted in FIG. 10. The roll can then be deployed across an optical detection region of the instrument, one sensor at a time. That is, as the film is advanced across the optical detection window, a probe light beam shines upon each sensor. The sensor can rest over the detection region for a period of time as such would be required to experience a positive pathogen-binding event, or to be eventually rendered ineffectual by nonspecific binding. The availability of a continuous roll of sensors allows an instrument to be deployed in the field for a long time interval, limited only by the size of the sensor roll and the contamination present in the local environment. These factors would influence the rate at which the sensor substrate is advanced. A substrate according to the film embodiment, may be virtually any length. Some may be characterized as having a length of at least about 5×, 10×, 100× the width.

C. Rotative Substrates

Film rolls are not the only possible embodiment of this invention, since the sensors could be deployed in virtually any arrangement. Other embodiments may include, but are not limited to, rotating platforms (e.g., disc, such as CD-ROM/DVD style formats) or carousel, or multi-sensor cartridges, etc, such as depicted in FIGS. 11A-D. Like on a CD or DVD, a rotating platform may have a series of optically sensitive sensor sites covering its entire surface, or for instance, may have a number of sensors along an edge of the disc carousel. As each sensor or group of sensors is exposed to the fluid (air or liquid) which may harbor analytes or toxins, the platform advances under the optical instrument detection window. In a more generalized characterization, applicable to both film and rotative embodiments herein, the substrates have an effective serial sensor length (i.e., the sum of the length of successive sensor regions over the entire substrate surface area) that totals up to about 1 m or 10 m long, or at least 10 m or 1 kilometer long.

Figure 12:
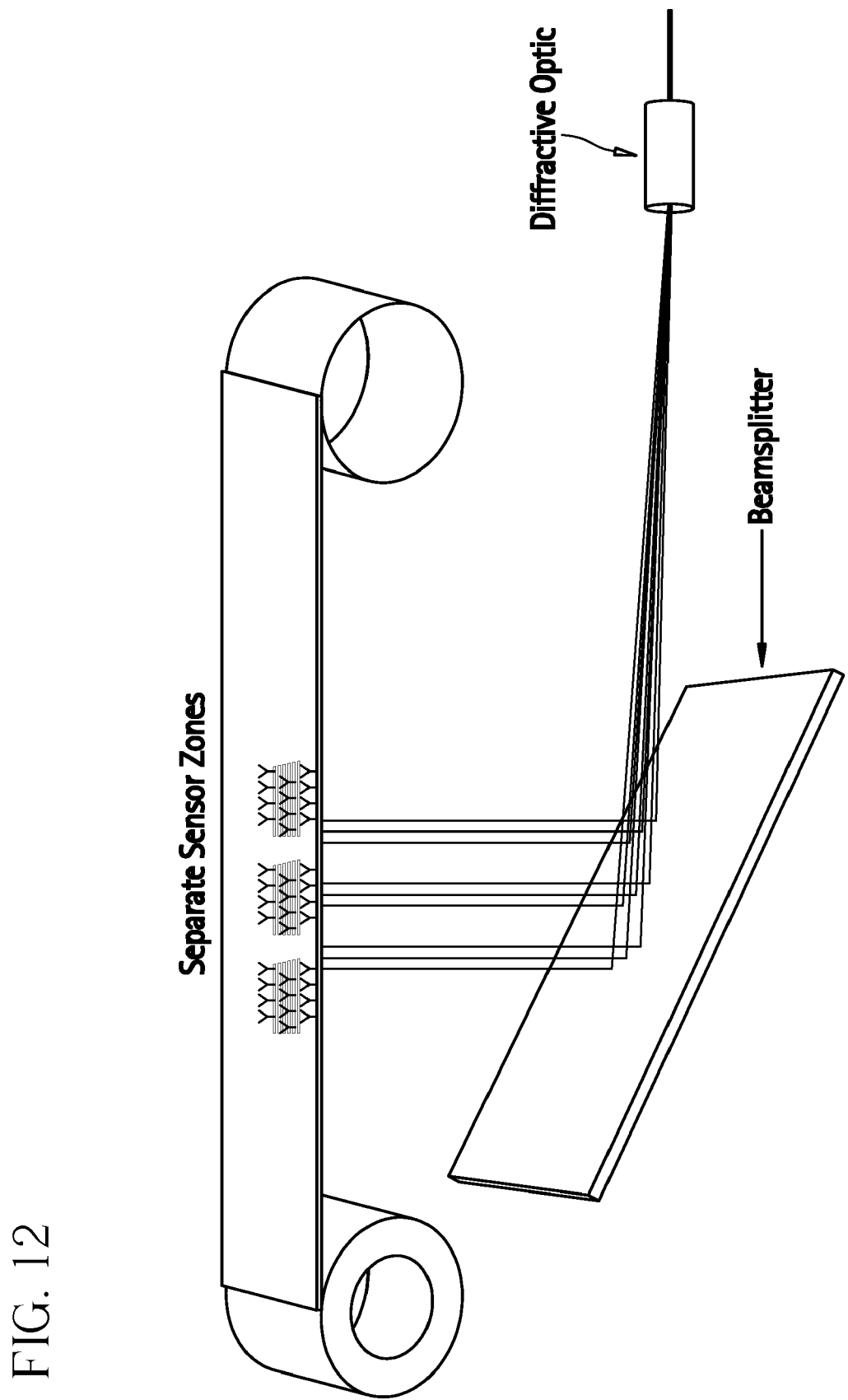
FIG. 12 depicts a multi-pathogen detection system according to the present invention.

As discussed above, one should be able to detect multiple toxins simultaneously in one instrument. Both film and rotative embodiments herein are equally applicable in this respect, because of the relatively small footprint of typical sensors (e.g., 9 mm$^2$). With several sensing regions arranged in proximity on the film, as depicted in FIG. 12, the optics can be modified to give simultaneous access to each sensing region (in this case accomplished with a diffractive optic). The optical multiplexing can be accomplished using a variety of additional methods, including optical fiber bundles, scanning mirrors, etc.

Sensors could be pre-fabricated in disposable cartridges containing one or more film or CD substrates, according to such embodiments, allowing easy maintenance of deployed sensing systems. A replacement or second cartridge may be inserted into place when all of the sensors on a first cartridge have been expended; thereby, ensuring a series of new sensors for prolonged continuous monitoring.

Section III—System Observations

The present evanescent-field sensor system may be applied to numerous uses for assaying a variety of biological or chemical molecules.

EXAMPLE 1

Figure 13:
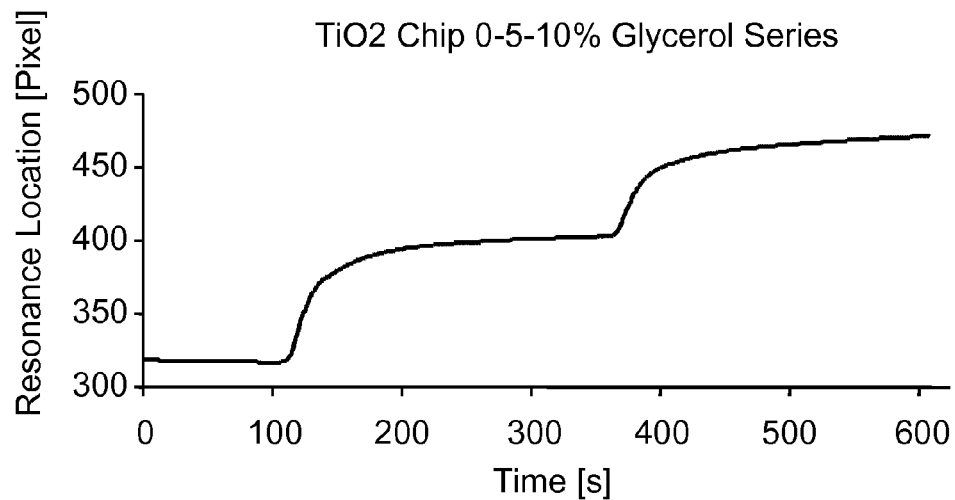
FIG. 13 shows the response of a GCW sensor as a function of the change in index of refraction due to the presence of chemical analyte.

One of the most basic demonstrations of evanescent sensor technology is the monitoring of the sensor response as chemicals with different refractive indices are flowed across the sensor surface. FIG. 13 illustrates the response of a single sensor to a changing chemical index of refraction at its surface. This operation is equivalent to the response that may accompany a chemical reaction on the sensor surface when an actual toxin encounters the chemo-reactive surface.

EXAMPLE 2

Figure 14:
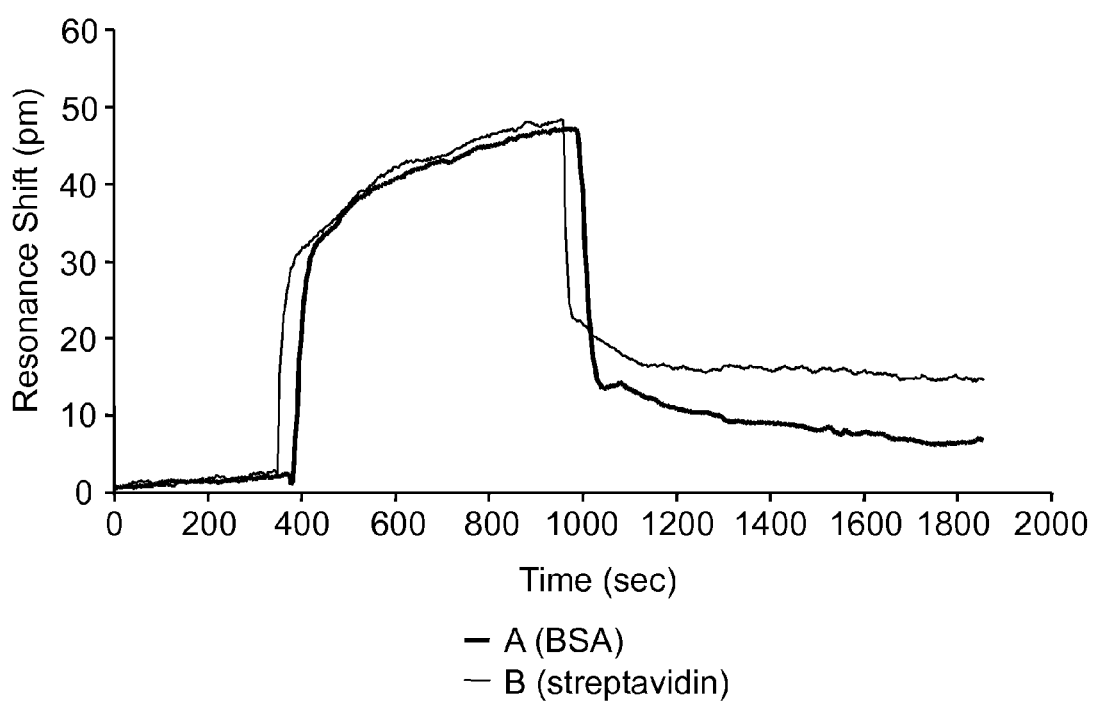
FIG. 14 shows the biological response of a GCW sensor for a bio-reactive vs. non bio-reactive surface.

As an example of biological reaction with a sensor surface, FIG. 14 demonstrates the difference in response between a bio-reactive and a non bio-reactive sensor. Curve A (BSA) represents a non-reactive chemistry, while curve B (streptavidin) indicates a bio-reactive one. Not only does this demonstrate the ability to sense the binding or reaction of biological species with a sensor, it also demonstrates the use of a control sensor to properly detect the desired toxins with good specificity.

EXAMPLE 3

Taking advantage of recently developed technology (Fang et al., "Ganglioside Microarrays for Toxin Detection," Langmuir 2003, 19, 1500-1505; U.S. Provisional Patent Application No. 60/392,275; and U.S. Patent Application Publication No. US2002/0094544 A1), arrays of micrometer-sized spots containing gangliosides may be fabricated within sensor regions. Ganglioside microarrays are robust, retaining their biological function and remaining associated with the substrate when drawn through an air/fluid interface. A different ganglioside compound (specific to a unique pathogen) may be immobilized on each separate sensor region of a substrate for simultaneous multi-pathogen detection according to the invention.

In FIG. 15, panels A-C show false images of three identical microarrays on a single γ-aminopropylsilane-(GAPS)-coated slide. Each microarray has three replicate microspots of DLPC (top row), DLPC doped with GM1 (middle row), and DLPC doped with GT1b (bottom row). GM1 is the target ganglioside for the cholera toxin, while GT1b is the target for tetanus. The first microarray (FIG. 15A) was treated with buffer only and serves as a negative control. As expected, no signal is observed on any of the microspots. The second microarray (FIG. 15B) was contacted with a cholera toxin (B subunit; FITC-CTx). Strong binding to microspots containing the GM1 ganglioside is observed. When the microarray was treated with a tetanus toxin (C fragment; FITC-TTx) (FIG. 15C), the highest amount of binding was found to correspond to microspots containing the GT1b ganglioside, in accordance with the known specificity of the toxin. Some FITC-TTx bound to the GM1 microspots—the signal is approximately 35% of that observed for binding to GT1b microspots (FIG. 15D).

EXAMPLE 4

Figure 16:
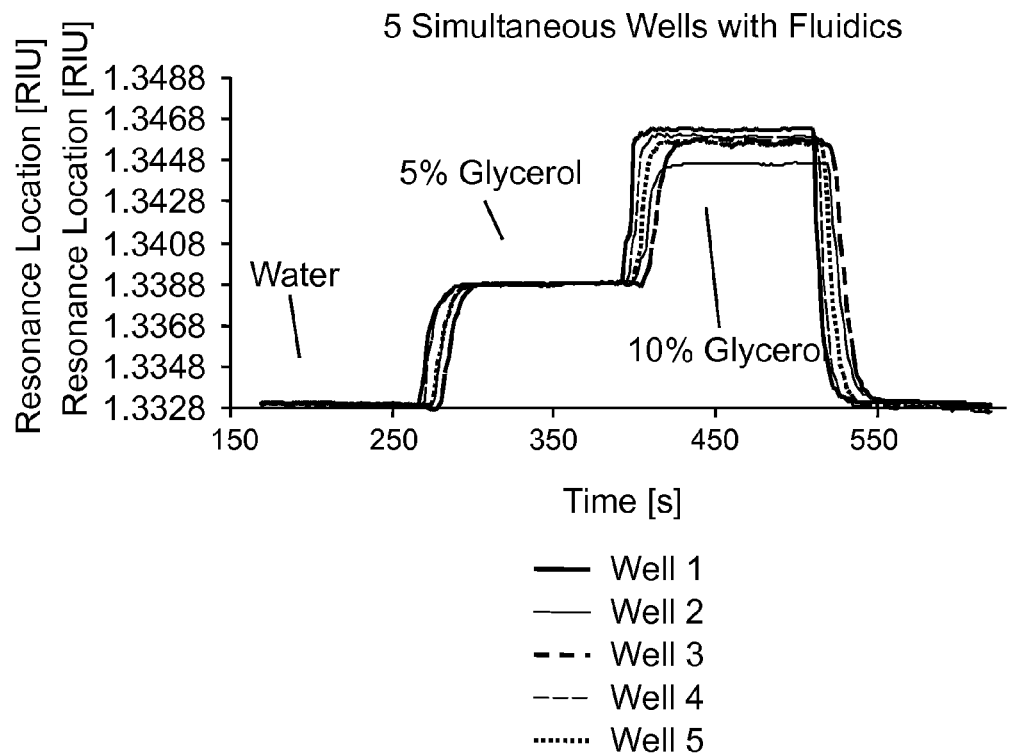
FIG. 16 is a graph depicting a multiplexed sensor operation with chemical refractive index differences.

FIG. 16 presents multiplexed operation of a GCW sensor, with five target sensing regions (in this case, within fluid wells). This data shows the ability to monitor multiple, individual sensors simultaneously and in real time. Each sensor's response for each unique fluid is clearly well above any noise (plateau deviation) or inter-sensor differences. This also demonstrates the ability to flow fluids past the sensors, in this case a liquid, in order to perform continuous monitoring.

EXAMPLE 5

Figure 17:
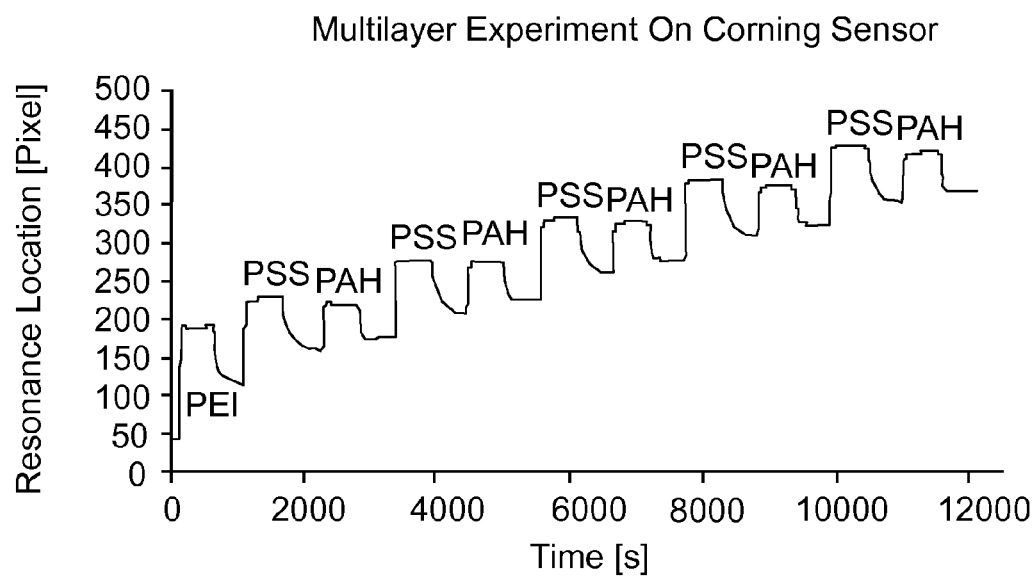
FIG. 17 is a graph showing real-time monitoring of PSS/PAH species. The sensors detect not only both species adsorbed to the surface, but also bulk ambient species near the surface within a few hundred nanometers.

An electrostatic multilayer experiment may be performed also on a GCW sensor with incorporated fluidics. Since PSS (polystyrene sulfonate) and PAH (polyallyamine hydrochloride), each of which is of an opposite electrostatic charge, form well-defined monolayers (~4 nm each), one can test quantitatively the surface sensitivity and dynamic range of the sensor itself. FIG. 17 summarizes test results for alternating layers of these compounds (where the initial PEI layer was used to activate the sensor surface for PSS/PAH binding).

FIG. 17 shows the benefits of real-time monitoring and the excellent dynamic range of an example instrument, allowing index variations from 1.333-1.400. The sensors can detect both PSS and PAH species that have adsorbed to the surface as well as bulk ambient species near the surface within a few hundred nanometers. When different chemicals are flowed over the sensors with either liquid (buffer or water) rinses in between, there are two types of sensor response. The first type is a bulk sensor response to the ambient chemical and the second type is a response to material adsorbed to the surface. This second contribution becomes evident only after rinsing, and quantified in the difference between the post-rinse level and the pre-exposure baseline level. The figure shows a multiple number of chemical-exposure/rinse cycles, and the cumulative adsorbed response level is calculated as the difference between successive rinses. In this manner, the FIG. 17 shows how evanescent sensors can respond to both bulk and adsorbed chemicals.

The present invention has been described in general and in detail by way of examples. Persons skilled in the art understand that the invention is not limited necessarily to the specific embodiments disclosed. Modifications and variations may be made without departing from the scope of the invention as defined by the following claims or their equivalents, including equivalent components presently known, or to be developed, which may be used within the scope of the present invention. Hence, unless changes otherwise depart from the scope of the invention, the changes should be construed as being included herein.

We claim:

1. A sensor system for detecting biological pathogens, chemical agents, or other harmful or toxic species, the sensor system comprises: 1) an evanescent-field sensor comprising a substrate with a surface covered at least in-part with a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; and 3) an air-fluid delivery system, comprising either macro or micro-fluidic passages designed to deliver biological or chemical analytes to at least a portion of said serially renewable sensing region, wherein said substrate having tensile strength and pliability can be supplied from a dispensing device as a single unit in a continuous fashion, and wherein said substrate being configurable to a fraction of its fully extended length along its longest dimension without breaking and can be retrieved from such configuration as a continuous body suitable for performing molecular interactive assays with the biological or chemical analytes to detect the biological pathogens, chemical agents, or other harmful or toxic species.

2. The sensor system according to claim 1, wherein said surface is modified with one or more materials, which enhance stable immobilization of said bio- or chemo-responsive layer.

3. The sensor system according to claim 1, wherein said surface has reactant and non-reactant regions.

4. The sensor system according to claim 1, wherein said evanescent-field sensor has a continuous substrate having thereon at least two or more contiguous sets of sensing regions, wherein each sensing region comprises a predetermined set of multiple regions for biological or chemical sensing.

5. The sensor system according to claim 4, wherein said contiguous sets of sensing regions are arranged longitudinally along the length of said substrate.

6. The sensor system according to claim 1, wherein said substrate is an optically transparent film of about 50 microns to about 2 mm thick.

7. The sensor system according to claim 1, wherein said bio- or chemo-responsive layer in each sensing region in said serially renewable sensing region is specifically formulated to react with particular biological pathogens, chemical agents, or other harmful or toxic species.

8. The sensor system according to claim 7, wherein each sensing region in said serially renewable sensing region is formulated to react with one or more particular biological pathogens, chemical agents, or other harmful or toxic species.

9. The sensor system according to claim 1, wherein said bio- or chemo-responsive layer includes a pathogen-specific antibody.

10. The sensor system according to claim 1, wherein said bio- or chemo-responsive layer is designed to adsorb a chemical molecule of interest.

11. The sensor system according to claim 1, wherein said bio- or chemo-responsive layer is designed to react with the biological pathogen, chemical agent, or other harmful or toxic species of interest resulting in either a change in mass or refractive index.

12. The sensor system according to claim 11, wherein said change in mass is due to either a binding of said biological pathogen, chemical agent, or other harmful or toxic species of interest, or a removal of an original chemistry from the surface.

13. The sensor system according to claim 1, wherein said evanescent-field sensor is able to detect biological toxins present in the biological or chemical analytes at levels of at least 1 femtomole per liter.

14. The sensor system according to claim 1, wherein said evanescent-field sensor is able to detect biological organism present in the biological or chemical analytes at levels of at least 1 organism per liter.

15. The sensor system according to claim 1, wherein said evanescent-field sensor is able to detect chemical toxins present in the biological or chemical analytes at levels of at least 50-70 attomoles per liter.

16. The sensor system according to claim 1, wherein said bio- or chemo-responsive layer has probes including a polymer matrix, a biomembrane with a ligand-gated ion channel, or chemical compounds.

17. The sensor system according to claim 1, wherein said bio- or chemo-responsive layer has probes including antibodies, or immuno-receptors.

18. The sensor system according to claim 1, wherein said evanescent-field sensor has the substrate coated with a metallic film capable of supporting surface plasmon modes.

19. The sensor system according to claim 1, wherein said substrate is made of either a ductile organic or inorganic material, or a combination of both.

20. The sensor system according to claim 19, wherein said ductile material is polymeric, amorphous, or metal.

21. The sensor system according to claim 1, wherein said pliable, continuous substrate takes a form like that of a ribbon, sheet, strip, tape, film, fiber, filament, or floss.

22. The sensor system according to claim 1, wherein said dispensing device includes a roll.

23. The sensor system according to claim 1, wherein said dispensing device is a reel.

24. The sensor system according to claim 1, wherein said pliable substrate has a plurality of perforations for engaging with sprockets.

25. The sensor system according to claim 1, wherein said substrate having a length that is at least about 5× the width.

26. The sensor system according to claim 1, wherein said substrate having a length that is at least about 10× the width.

27. The sensor system according to claim 1, wherein said substrate having a length that is at least about 100× the width.

28. The sensor system according to claim 1, wherein said continuous substrate has an effective serial sensor up to 1 m long.

29. The sensor system according to claim 1, wherein said continuous substrate has an effective serial sensor length of up to 10 m long.

30. The sensor system according to claim 1, wherein said continuous substrate has an effective serial sensor length of at least 10 m long.

31. The sensor system according to claim 1, wherein said continuous substrate has an effective serial sensor length of at least 1 kilometer long.

32. The sensor system according to claim 1, wherein said evanescent-field sensor, said optical interrogation apparatus, said air-fluid delivery system, said dispensing device are deployed on a mobile platform and moved to or through a contaminated environment and sensor response signals are transmitted to a remote analysis location.

33. A sensor system for detecting biological pathogens, chemical agents, or other harmful or toxic species, the sensor system comprises: 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; 3) an air-fluid delivery system, comprising either macro or micro-fluidic passages designed to deliver biological or chemical analytes to at least a portion of said serially renewable sensing region, wherein said substrate is in the form of a rotatable platform.

34. A sensor system for detecting biological pathogens, chemical agents, or other harmful or toxic species, the sensor system comprises: 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument 3) an air-fluid delivery system, comprising either macro or micro-fluidic passages designed to deliver biological or chemical analytes to at least a portion of said serially renewable sensing region 4) said bio- or chemo-responsive layer in said serially renewable sensing region is specifically formulated to react with particular biological or chemical analytes; and 5) said bio- or chemo-responsive layer includes a pathogen-specific ganglioside probe.

35. The sensor system according to claim 34, wherein said evanescent-field sensor further comprising a collection of individual substrates, each having one or more sensing regions that can be optically interrogated in series.

36. A sensor system for detecting biological pathogens, chemical agents, or other harmful or toxic species, the sensor system comprises: 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; 3) an air-fluid delivery system, comprising either macro or micro-fluidic passages designed to deliver biological or chemical analytes to at least a portion of said serially renewable sensing region; and (4) said bio- or chemo-responsive layer has probes including glycolipids, gangliosides, or lipid biomembranes.

37. A sensor system for detecting biological pathogens, chemical agents, or other harmful or toxic species, the sensor system comprises: 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; 3) an air-fluid delivery system, comprising either macro or micro-fluidic passages designed to deliver biological or chemical analytes to at least a portion of said serially renewable sensing region; and 4) said substrate has immobilized antibodies against various different surface marker molecules of a particular pathogen.

38. The sensor system according to claim 37, wherein antibodies include 4-5 different antibodies for anthrax.

39. A sensor system for detecting biological pathogens, chemical agents, or other harmful or toxic species, the sensor system comprises; 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; 3) an air-fluid delivery system, comprising either macro or micro-fluidic passages designed to deliver biological or chemical analytes to at least a portion of said serially renewable sensing region, wherein said evanescent-field sensor has a waveguiding structure formed by an effective index waveguiding region covering the substrate, wherein the waveguiding region has a refractive index at least 0.1% higher than the refractive index of the substrate; a diffraction grating contained in or near the waveguiding structure; and the bio- or chemo-responsive layer covering the waveguiding region, wherein said bio- or chemo-responsive layer is capable of interacting with the biological pathogen, chemical agent, or other harmful or toxic species of interest.

40. A sensor system for detecting biological pathogens, chemical agents, or other harmful or toxic species, the sensor system comprises; 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; 3) an air-fluid delivery system, comprising either macro or micro-fluidic passages designed to deliver biological or chemical analytes to at least a portion of said serially renewable sensing region; and 4) said evanescent-field sensor has the substrate coated with multiple dielectric layers, having varying optical indices, in which an optical field has an evanescent tail extending beyond the layer immediately in contact with a medium to be sensed.

41. A sensor system for detecting biological pathogens, chemical agents, or other harmful or toxic species, the sensor system comprises; 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; 3) an air-fluid delivery system, comprising either macro or micro-fluidic passages designed to deliver biological or chemical analytes to at least a portion of said serially renewable sensing region; and 4) said evanescent-field sensor is a patterned optical circuit.

42. A sensor system for detecting biological pathogens, chemical agents, or other harmful or toxic species, the sensor system comprises; 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; 3) an air-fluid delivery system, comprising either macro or micro-fluidic passages designed to deliver biological or chemical analytes to at least a portion of said serially renewable sensing region; and 4) said evanescent-field sensor is an interferometer.

43. A sensor system for detecting biological pathogens, chemical agents, or other harmful or toxic species, the sensor system comprises; 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; 3) an air-fluid delivery system, comprising either macro or micro-fluidic passages designed to deliver biological or chemical analytes to at least a portion of said serially renewable sensing region; and 4) said evanescent-field sensor is a Mach-Zehnder interferometer.

44. A sensor system for detecting biological pathogens, chemical agents, or other harmful or toxic species, the sensor system comprises; 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; 3) an air-fluid delivery system, comprising either macro or micro-fluidic passages designed to deliver biological or chemical analytes to at least a portion of said serially renewable sensing region; and (4) the optical delivery system includes a diffraction grating, a prism, or a specifically tailored dielectric stack in order to couple incoming and out-going optical probe beams to said evanescent-field sensor.

45. A sensor system for detecting biological pathogens, chemical agents, or other harmful or toxic species, the sensor system comprises; 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; 3) an air-fluid delivery system, comprising either macro or micro-fluidic passages designed to deliver biological or chemical analytes to at least a portion of said serially renewable sensing region; and (4) the optical delivery system utilizes optical fiber to either deliver or collect a light signal from said evanescent-field sensor.

46. The sensor system according to claim 45, wherein the optical delivery system includes a diffractive optic to generate multiple optical probe beams for multiplexed monitoring of multiple sensing regions.

47. A sensor system for detecting biological pathogens, chemical agents, or other harmful or toxic species, the sensor system comprises; 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; 3) an air-fluid delivery system, comprising either macro or micro-fluidic passages designed to deliver biological or chemical analytes to at least a portion of said serially renewable sensing region; 4) said evanescent-field sensor has a continuous substrate having thereon at least two or more contiguous sets of sensor arrays, wherein each sensor array comprises a predetermined set of multiple regions for biological or chemical sensing; and 5) said contiguous sets of sensor arrays comprise families of toxin probes.

48. A sensor system for detecting biological pathogens, chemical agents, or other harmful or toxic species, the sensor system comprises; 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; 3) an air-fluid delivery system, comprising either macro or micro-fluidic passages designed to deliver biological or chemical analytes to at least a portion of said serially renewable sensing region; 4) said surface has reactant and non-reactant regions; and 5) said surface has contiguous set of arrays of toxin targets are repeating along the length of said substrate and each of said set of arrays of toxin targets is recognizably separated from one another.

49. The sensor system according to claim 48, wherein each of said arrays of toxin targets is indexed according to an identifier.

50. The sensor system according to claim 49, wherein said identifier may include a biological marker, a chemical marker, an alpha-numeric label, or a bar code.

51. The sensor system according to claim 50, wherein said bar code is optical, electronic, metallic, or magnetic.

52. A sensor system for detecting biological pathogens, chemical agents, or other harmful or toxic species, the sensor system comprises; 1) an evanescent-field sensor comprising a substrate with a surface covered at least in-part a bio- or chemo-responsive layer which forms a serially renewable sensing region; 2) an optical interrogation apparatus for monitoring at least a portion of said bio- or chemo-responsive layer, said optical interrogation apparatus comprising a light source, an optical delivery system, and a detection instrument; 3) an air-fluid delivery system, comprising either macro or micro-fluidic passages designed to deliver biological or chemical analytes to at least a portion of said serially renewable sensing region; and 4) said substrate has a length, width, and thickness compatible with commercial 35-mm photographic film technology.

* * * * *

UNITED STATES PATENT AND TRADEMARK OFFICE
CERTIFICATE OF CORRECTION

PATENT NO.       : 7,368,281 B2
APPLICATION NO.  : 10/794937
DATED            : May 6, 2008
INVENTOR(S)      : Eric J. Mozdy et al.

It is certified that error appears in the above-identified patent and that said Letters Patent is hereby corrected as shown below:

| No. | Col. | Line | Description |
|---|---|---|---|
| 1 | 6 | 9 | Please delete "inmuobilized" and replace with "immobilized". |
| 2 | 7 | 25 | Please delete "enviromnental" and replace with "environmental". |
| 4 | 16 | 20 | Please delete "70" and replace with "100". |

Signed and Sealed this

Seventeenth Day of March, 2009

JOHN DOLL
*Acting Director of the United States Patent and Trademark Office*